(12) United States Patent
Coe et al.

(10) Patent No.: US 9,375,252 B2
(45) Date of Patent: Jun. 28, 2016

(54) ADJUSTABLE LENGTH AND/OR EXPOSURE ELECTRODES

(71) Applicant: COVIDIEN LP, Mansfield, MA (US)

(72) Inventors: Jonathan A. Coe, Menlo Park, CA (US); Casey M. Ladtkow, Erie, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 13/949,381

(22) Filed: Jul. 24, 2013

(65) Prior Publication Data

US 2014/0039481 A1 Feb. 6, 2014

Related U.S. Application Data

(60) Provisional application No. 61/678,808, filed on Aug. 2, 2012.

(51) Int. Cl.
*A61B 18/14* (2006.01)
*A61B 18/18* (2006.01)
(Continued)

(52) U.S. Cl.
CPC ............. *A61B 18/14* (2013.01); *A61B 18/1477* (2013.01); *A61B 18/18* (2013.01); *A61B 2017/00991* (2013.01); *A61B 2017/347* (2013.01); *A61B 2018/00023* (2013.01); *A61B 2018/00172* (2013.01); *A61B 2018/00178* (2013.01); *A61B 2018/00196* (2013.01);
(Continued)

(58) Field of Classification Search
CPC ........ A61B 18/04; A61B 18/08; A61B 18/10; A61B 18/12; A61B 18/14; A61B 18/148; A61B 18/1482; A61B 18/1485; A61B 18/1487; A61B 18/18; A61B 18/1815; A61B 2018/00011; A61B 2018/00029; A61B 2018/00077; A61B 2018/00577; A61B 2018/00791; A61B 2018/00702; A61B 2018/1425; A61B 5/1473; A61B 5/14865; A61B 2218/002
USPC ............................. 606/27–29, 39–41, 44–49; 607/101–102
See application file for complete search history.

(56) References Cited

U.S. PATENT DOCUMENTS

D223,367 S 4/1972 Kountz
D263,020 S 2/1982 Rau, III
(Continued)

FOREIGN PATENT DOCUMENTS

CN 1103807 A 6/1995
DE 390937 C 3/1924
(Continued)

OTHER PUBLICATIONS

U.S. Appl. No. 13/419,981, filed Mar. 14, 2012, Joseph D. Brannan.
(Continued)

*Primary Examiner* — Michael Peffley
*Assistant Examiner* — Khadijeh Vahdat (57) ABSTRACT

An ablation system is provided. The ablation system includes an ablation device having a handle assembly and an electrode assembly. The handle assembly includes a housing configured for operable engagement by a user. The electrode assembly includes a tubular electrode having an open proximal end and a closed distal end. The tubular electrode is movable relative to the housing to adjust an insertable length of the electrode assembly.

10 Claims, 9 Drawing Sheets

(51) Int. Cl.
　　　*A61B 17/00*　　　　　(2006.01)
　　　*A61B 17/34*　　　　　(2006.01)
　　　*A61B 18/00*　　　　　(2006.01)
(52) U.S. Cl.
　　　CPC .............. *A61B2018/00202* (2013.01); *A61B 2018/00529* (2013.01); *A61B 2018/00541* (2013.01); *A61B 2018/00577* (2013.01); *A61B 2018/00791* (2013.01); *A61B 2018/1435* (2013.01); *A61B 2018/1467* (2013.01)

(56) References Cited

U.S. PATENT DOCUMENTS

| | | | |
|---|---|---|---|
| D266,842 S | 11/1982 | Villers et al. | |
| D278,306 S | 4/1985 | McIntosh | |
| 4,565,200 A * | 1/1986 | Cosman | A61B 18/1477 600/373 |
| D295,893 S | 5/1988 | Sharkany et al. | |
| D295,894 S | 5/1988 | Sharkany et al. | |
| 4,919,129 A | 4/1990 | Weber, Jr. et al. | |
| 5,234,429 A * | 8/1993 | Goldhaber | 606/45 |
| 5,318,565 A | 6/1994 | Kuriloff et al. | |
| D354,218 S | 1/1995 | Van de Peer | |
| 5,458,597 A | 10/1995 | Edwards et al. | |
| 5,496,314 A | 3/1996 | Eggers | |
| 5,693,044 A * | 12/1997 | Cosmescu | 606/42 |
| 5,762,626 A | 6/1998 | Lundquist et al. | |
| 5,893,863 A | 4/1999 | Yoon | |
| 5,993,447 A * | 11/1999 | Blewett | A61B 18/1477 600/105 |
| D424,693 S | 5/2000 | Pruter | |
| D424,694 S | 5/2000 | Tetzlaff et al. | |
| D425,201 S | 5/2000 | Tetzlaff et al. | |
| 6,099,525 A | 8/2000 | Cosmescu | |
| 6,142,995 A | 11/2000 | Cosmescu | |
| 6,197,024 B1 * | 3/2001 | Sullivan | 606/45 |
| 6,241,725 B1 | 6/2001 | Cosman | |
| D449,886 S | 10/2001 | Tetzlaff et al. | |
| 6,355,034 B2 | 3/2002 | Cosmescu | |
| D457,958 S | 5/2002 | Dycus et al. | |
| D457,959 S | 5/2002 | Tetzlaff et al. | |
| 6,458,125 B1 | 10/2002 | Cosmescu | |
| 6,464,661 B2 | 10/2002 | Edwards et al. | |
| D487,039 S | 2/2004 | Webster et al. | |
| 6,702,812 B2 | 3/2004 | Cosmescu | |
| D496,997 S | 10/2004 | Dycus et al. | |
| D499,181 S | 11/2004 | Dycus et al. | |
| D525,361 S | 7/2006 | Hushka | |
| 7,077,842 B1 * | 7/2006 | Cosman | 606/41 |
| 7,112,199 B2 | 9/2006 | Cosmescu | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| D564,662 S | 3/2008 | Moses et al. | |
| D576,932 S | 9/2008 | Strehler | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| D634,010 S | 3/2011 | DeCarlo | |
| 7,935,109 B2 | 5/2011 | Cosmescu | |
| 8,280,525 B2 | 10/2012 | Rusin et al. | |
| D681,810 S | 5/2013 | Decarlo | |
| 2006/0178666 A1 * | 8/2006 | Cosman et al. | 606/41 |
| 2007/0049922 A1 * | 3/2007 | Rontal | 606/41 |
| 2009/0118727 A1 * | 5/2009 | Pearson et al. | 606/41 |
| 2011/0306969 A1 * | 12/2011 | Coe et al. | 606/41 |
| 2012/0116397 A1 | 5/2012 | Rencher et al. | |
| 2013/0041362 A1 | 2/2013 | Lee et al. | |
| 2014/0052131 A1 * | 2/2014 | Busch-Madsen | A61B 18/1477 606/41 |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 90 06 694 U1 | 8/1990 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 648 515 A1 | 4/1995 |
| EP | 0 836 868 A2 | 4/1998 |
| EP | 0 882 955 A1 | 12/1998 |
| EP | 1 159 926 A2 | 12/2001 |
| EP | 1 870 052 A2 | 12/2007 |
| EP | 2 322 111 A1 | 5/2011 |
| EP | 2322111 A1 | 5/2011 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |

(56) References Cited

FOREIGN PATENT DOCUMENTS

| | | | |
|---|---|---|---|
| JP | 2001003776 A | 1/2001 | |
| JP | 2001008944 A | 1/2001 | |
| JP | 2001029356 A | 2/2001 | |
| JP | 2001037775 A | 2/2001 | |
| JP | 2001128990 A | 5/2001 | |
| JP | 2001231870 A | 8/2001 | |
| JP | 2008142467 A | 6/2008 | |
| KR | 20070093068 A | 9/2007 | |
| KR | 20100014406 A | 2/2010 | |
| KR | 20120055063 A | 5/2012 | |
| SU | 166452 | 11/1964 | |
| SU | 401367 A1 | 10/1973 | |
| SU | 727201 A2 | 4/1980 | |
| WO | 9901074 A1 | 1/1999 | |
| WO | 00/36985 A2 | 6/2000 | |
| WO | 2010/035831 A1 | 4/2010 | |
| WO | 2010035839 A2 | 4/2010 | |
| WO | WO2012155922 | * 5/2012 | ............ A61B 18/14 |

OTHER PUBLICATIONS

U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. Decarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,320, filed May 22, 2012, Joseph D. Brannan.
U.S. Appl. No. 13/711,086, filed Dec. 11, 2012, Joseph D. Brannan.
U.S. Appl. No. 13/835,183, filed Mar. 15, 2013, Arts.
U.S. Appl. No. 13/835,513, filed Mar. 15, 2013, Brannan.
U.S. Appl. No. 13/836,014, filed Mar. 15, 2013, Arts.
U.S. Appl. No. 13/836,353, filed Mar. 15, 2013, Arts.
U.S. Appl. No. 13/839,562, filed Mar. 15, 2013, Zheng.
U.S. Appl. No. 13/867,834, filed Jul. 22, 2013, Brannan.
U.S. Appl. No. 13/871,142, filed Apr. 26, 2013, Ohri.
U.S. Appl. No. 13/886,080, filed May 2, 2013, Bahney.
U.S. Appl. No. 13/889,989, filed May 8, 2013, Lee.
U.S. Appl. No. 13/903,668, filed May 28, 2013, Podhajsky.
U.S. Appl. No. 13/904,478, filed May 29, 2013, Ohri.
U.S. Appl. No. 13/908,463, filed Jun. 3, 2013, Brannan.
U.S. Appl. No. 13/908,555, filed Jun. 3, 2013, Dunning.
U.S. Appl. No. 13/920,367, filed Jun. 18, 2013, Sharonov.
U.S. Appl. No. 13/920,411, filed Jun. 18, 2013, Sharonov.
U.S. Appl. No. 13/922,006, filed Jun. 19, 2013, Nau.
U.S. Appl. No. 13/942,833, filed Jul. 16, 2013, Sharonov.
U.S. Appl. No. 13/942,864, filed Jul. 16, 2013, Sharonov.
U.S. Appl. No. 13/943,452, filed Jul. 16, 2013, Behnke.
U.S. Appl. No. 13/945,519, filed Jul. 18, 2013, Prakash.
U.S. Appl. No. 13/945,718, filed Jul. 18, 2013, Rossetto.
U.S. Appl. No. 13/957,087, filed Aug. 1, 2013, Brannan.
U.S. Appl. No. 13/973,543, filed Aug. 22, 2013, Orszulak.
U.S. Appl. No. 14/011,414, filed Aug. 27, 2013, Ohri.
U.S. Appl. No. 14/011,438, filed Aug. 27, 2013, Ohri.
U.S. Appl. No. 14/014,937, filed Aug. 30, 2013, Willyard.
U.S. Appl. No. 14/017,995, filed Sep. 4, 2013, Brannan.
U.S. Appl. No. 14/018,081, filed Sep. 4, 2013, Brannan.
LigaSureTM Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSureTM Vessel Sealing System and LigaSureTM Atlas 20 cm Open Instrument" Innovations That Work, Jun. 2003.
Muller et al., "Extended Left Hemicolectomy Using the LigaSureTM Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences—Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSureTM versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSureTM Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.

(56) References Cited

OTHER PUBLICATIONS

Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.—Medical Professionals: TargisTM Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
U.S. Appl. No. 08/136,098, filed Oct. 14, 1993, Roger A. Stern.
U.S. Appl. No. 08/483,742, filed Jun. 7, 1995, Roger A. Stern.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. T Heniford M.D. et al., "Initial Research and Clinical Results with an Electrothermal Bipolar Vessel Sealer" Oct. 1999.

Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSureTM" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSureTM Vessel Sealing System: A Case Report" Innovations That Work, Feb. 2002.
Humphries Jr. et al., "Finite-Element Codes to Model Electrical Heating and Non-Llnear Thermal Transport in Biological Media", Proc. ASME HTD-355, 131 (1997).

(56) References Cited

OTHER PUBLICATIONS

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Jarrett et al., "Use of the LigaSureTM Vessel Sealing System for Peri-Hilar Vessels in Laparoscopic Nephrectomy" Sales/Product Literature 2000.

Johnson et al., "Evaluation of a Bipolar Electrothermal Vessel Sealing Device in Hemorrhoidectomy" Sales/Product Literature, Jan. 2004.

Johnson, "Evaluation of the LigaSureTM Vessel Sealing System in Hemorrhoidectormy" American College of Surgeons (ACS) Clinic La Congress Poster (2000).

Johnson et al., "New Low-Profile Applicators for Local Heating of Tissues", IEEE Transactions on Biomedical Engineering, vol., BME-31, No. 1, Jan. 1984, pp. 28-37.

Johnson, "Use of the LigaSureTM Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, "LigaSureTM System Used in Laparoscopic 1st and 2nd Stage Orchiopexy" Innovations That Work, Nov. 2002.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

Extended European Search Report corresponding to EP 13 17 8896, dated Dec. 5, 2013; 10 pages.

European Communication and Examination Report, issued Apr. 10, 2015, corresponding to European Application No. 13 178 896.0; 8 pages.

European Communication dated Aug. 11, 2015, corresponding to European Patent Application No. 13178896.0; 5 pages.

\* cited by examiner

ADJUSTABLE LENGTH AND/OR EXPOSURE ELECTRODES

CROSS REFERENCE TO RELATED APPLICATION

The present application claims the benefit of and priority to U.S. Provisional Application Ser. No. 61/678,808, filed on Aug. 2, 2012, the entire contents of which are incorporated herein by reference.

BACKGROUND

1. Technical Field

The present disclosure relates to radiofrequency ablation devices. More particularly, the present disclosure relates to radiofrequency ablation devices having an adjustable insertable length and/or an adjustable exposed length.

2. Background of Related Art

Radiofrequency ablation (RFA) is a therapy commonly used for the treatment of solid tumors in the liver and lung. Typically, devices configured for RFA are intended for coagulation of tissue during percutaneous, laparoscopic, and open surgical procedures. Such devices produce local tissue heating at the tip of an active electrode using radiofrequency current applied between the active electrode needle and grounding pads, resulting in a defined volume of tissue necrosis (also referred to as an 'ablation'). Some of these devices include a system that circulates chilled water through the electrode to control the tissue impedance at the electrode surface, allowing for increased energy deposition into surrounding tissue. Once such system is provided in the Cool-Tip™ RF System E Series available from Covidien of Boulder, Colo.

Generally, the RFA devices are provided to a clinician with multiple active electrodes of various configurations. The electrodes are identifiable primarily by the overall length of the insertable portion of the electrode and the length of the exposed portion of the electrode through which RF energy is delivered to tissue. Providing electrodes of different lengths allows physicians to access a variety of locations within the body and in patients having different body habitus. For example, in obese patients, it is desirable to provide longer active electrodes, as the insertable portion must often pass through layers of subcutaneous fat that can commonly be 5"-6" thick. Though a longer active electrode length (e.g., 25 cm) would be preferable for such patients, such a length would be unwieldy for thinner patients. Providing electrodes of different exposure lengths allows physicians to control the geometry of the ablation. A shorter exposure length (e.g., 7 mm) results in a shorter axis, smaller ablation, while a larger exposure length (e.g., 4 cm) results in a taller axis, larger ablation. The exposure effectively limits the amount of RF energy that can be delivered via the active electrode, much like a camera's aperture limits the amount of light that reaches the photographic film.

Numerous active electrodes are required to provide a clinician with an electrode having both the correct combination of desired insertable length and desired exposed length. Providing the numerous active electrodes of various lengths is costly, and since only a couple of the numerous active electrodes will likely be used during a procedure, providing numerous active electrodes is also wasteful.

SUMMARY

Accordingly, an improved ablation system is provided. The ablation system includes an ablation device having a handle assembly and an electrode assembly. The handle assembly includes a housing configured for operable engagement by a user. The electrode assembly includes a tubular electrode having an open proximal end and a closed distal end. The tubular electrode is movable relative to the housing to adjust an insertable length of the electrode assembly.

In one embodiment, the housing of the ablation device is configured for operable connection with a cooling assembly. The tubular electrode may be configured for operable connection with a source of radio-frequency energy. The ablation device may further include a locking mechanism for selectively securing the tubular electrode relative to the housing. The locking assembly may include a spring and a ball, the spring configured to bias the ball into one of a plurality of detents formed along the tubular electrode. The system may further include a coolant source and a power source. Alternatively, or in addition, the system includes a temperature monitor and a microprocessor. The handle assembly may form a pencil grip or a pistol grip. In some embodiment, the handle assembly is configured for operable engagement with a trocar assembly.

An alternative ablation device is also provided. The ablation device includes a handle assembly and an electrode assembly. The handle assembly defines a longitudinal axis and includes at least a first housing section and a second housing section. The electrode assembly is operably connected to the handle assembly. The second housing section is slidably disposed relative to the first housing section and the electrode assembly. In one embodiment, the handle assembly further includes a third housing section slidably disposed relative to the second housing section and the electrode assembly.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Embodiments of the present disclosure relate to radio-frequency ablation (RFA) devices having an electrode with an adjustable insertable length and/or an electrode with an adjustable exposed length. Other embodiments of the present disclosure relate to modifications to ablation devices to simply the devices and/or reduce costs of manufacturing and using the devices. In a device having an electrode with an adjustable insertable length, the electrode may be selectively movable relative to a housing of the device and may include a mechanism for securing the electrode with a given insertable length. Alternatively, the housing of the ablation device may be selectively movable relative to the electrode to provide a device having an electrode with an adjustable insertable length. The housing may include a locking mechanism for securing the housing such that the electrode has a desired insertable length. In a device having an adjustable exposed length, a protective layer may be selectively movable relative to the electrode to selectively expose or cover the electrode.

Figure 1:
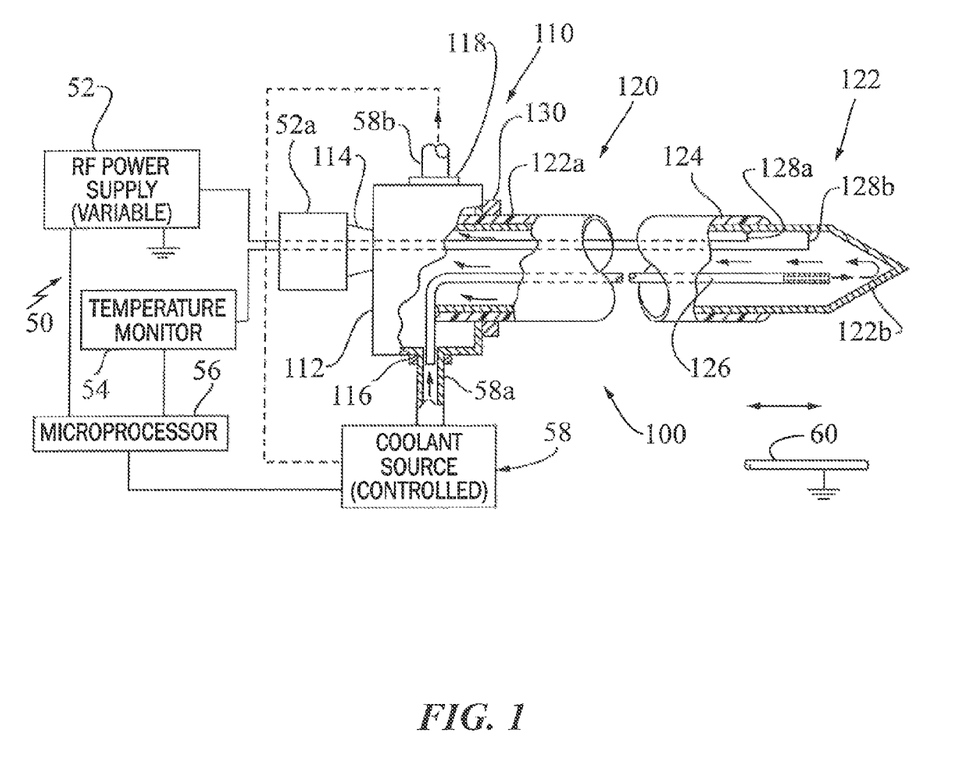
FIG. 1 is a schematic of an ablation system including an ablation device in accordance with an embodiments of the present disclosure.

With reference to FIG. 1, an ablation system according to an embodiment of the present disclosure is shown generally ablation system 50. Ablation system 50 includes a radio-frequency ablation device 100, a power source 52 for providing radio-frequency power to ablation device 100, a temperature monitor 54 for monitoring the temperature of electrode 122 of ablation device 100, a coolant source 58 for circulating a continuous supply of cooling fluid through ablation device 100, a microprocessor 56 for controlling the delivery of power from power source 52 and/or the flow of coolant from coolant source 58, and a patient return pad 60 configured for operable connection between a patient (not shown) and power source 52. Ablation system 50 will only be described to the extent necessary to fully disclose the aspects of the present disclosure. For a more detailed discussion of the structure and function of ablation system 50 please refer to commonly owned U.S. Pat. Nos. 6,506,189 and 6,575,969, the contents of which are incorporated herein by reference in their entirety.

Figure 8:
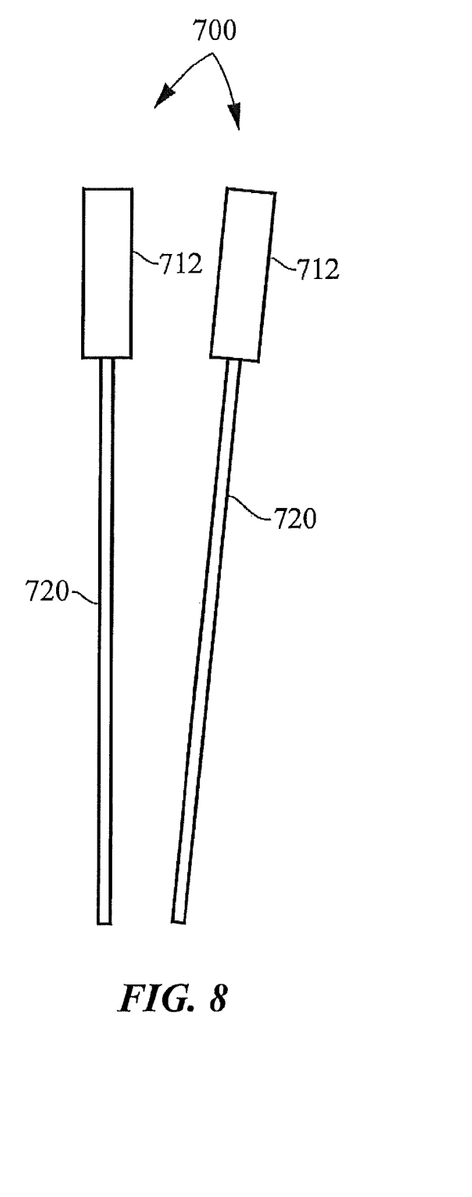
FIG. 8 is a side view of a pair of ablation devices in accordance with an embodiment of the present disclosure.
Figures 10, 10A:
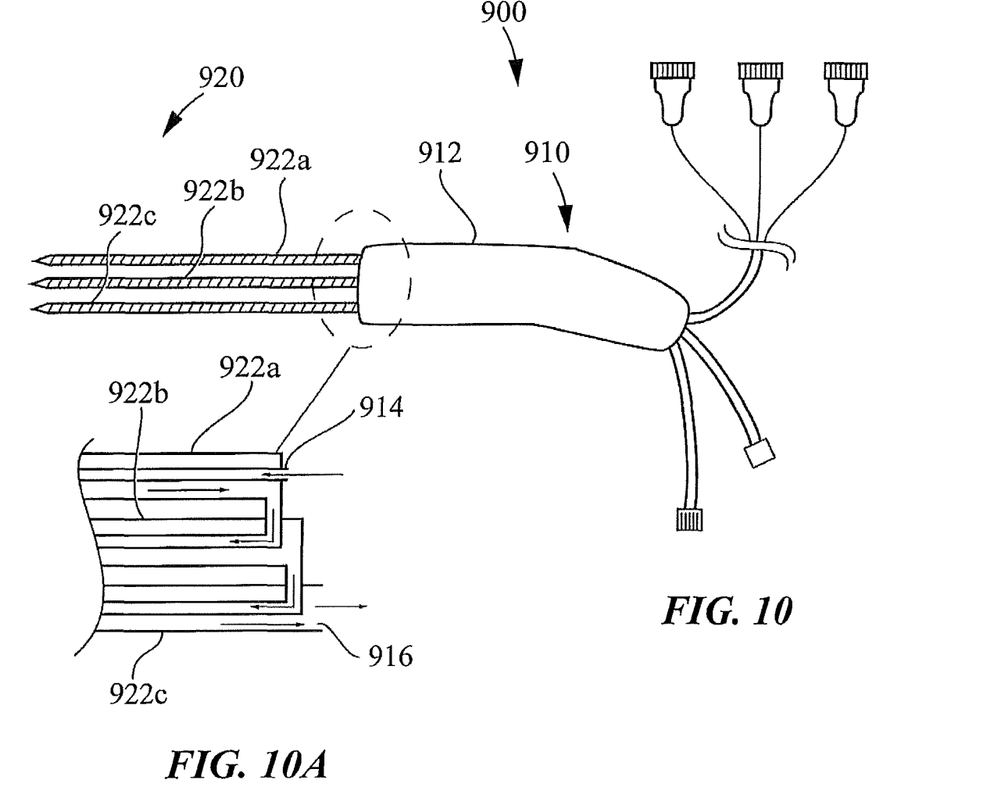
FIG. 10 is a side view of an ablation device according to still yet another embodiment of the present disclosure having a multiple electrode assembly.
FIG. 10A is an enlarged internal view of the proximal end of the multiple electrode assembly of FIG. 10.

With continued reference to FIG. 1, radio-frequency ablation device 100 includes a handle assembly 110 and an electrode assembly 120. Handle assembly 110 includes a housing or hub 112. As shown, housing 112 is configured for engagement with a trocar assembly or other access device. In other embodiments, housing 112 may be configured for hand-held use, i.e., housing 212 (FIG. 2) and/or for use with multiple electrodes wherein each of the electrodes includes a separate housing, i.e., housing 712 (FIG. 8), or the multiple electrodes extend from the same housing, i.e., housing 912 (FIG. 10). Housing 112 is configured for operable connection with power source 52 and coolant source 58. In particular, housing 112 includes an electrical port 114 for operable connection with a plug 52a of power supply 52, an inlet port 116 for fluid communication with a supply line 58a of coolant source 58, and an outlet port 118 for fluid communication with a return line 58b of coolant source 58. Electrode assembly 120 includes a tubular electrode 122 having an open proximal end 122a and a closed distal end 122b. Electrode assembly 120 further includes an insulative coating or protective layer 124 disposed about a length of tubular electrode 122 for preventing contact between electrode 122 and tissue remote from the target site. The portion of tubular electrode 122 that is not covered by insulative coating 124 is the exposed portion of tubular electrode 122. The insertable length of electrode assembly 120 is that portion of electrode assembly 120 that is configured to be received through tissue. The insertable length of electrode assembly may include protective layer 124. As shown in FIG. 1, the insertable length of electrode assembly 120 is that portion of electrode assembly 120 that extends distally of housing 112.

Still referring to FIG. 1, a supply tube 126 extends substantially the length of tubular electrode 122 to provide a cooling fluid to exposed distal end 122b. As seen in FIG. 1, in operation, cooling fluid from coolant source 58 is directed through supply tube 126 to exposed distal end 122b of tubular electrode 122. The cooling fluid then flows back through tubular electrode 122 and exits ablation device 100 through outlet port 118. A pair of wires 128a, 128b operably connect exposed distal end 122b of tubular electrode 122 with electrical port 114. As will be discussed in further detail below, tubular electrode 122 may be configured to be selectively extendable relative to housing 112 to adjust the overall length of the insertable portion of electrode assembly 120. As will also be discussed in further detail below, protective layer 124 may also be selectively extendable relative to tubular electrode 122 to adjust the exposed length of electrode 122. Housing 110 and/or electrode assembly 120 may include a locking mechanism 130 for selectively locking tubular electrode 122 and/or protective layer 124 relative to each other and/or housing 112.

The following disclosure will describe various mechanisms for selectively adjusting the insertable length of the electrode and/or selectively adjusting the exposed length of the electrode. Similar elements will be identified with similar reference characters throughout the embodiments. It should be understood that similar structures of the embodiments will only be described in sufficient detail to fully disclose the specific embodiments and that the structures may be interchangeable throughout the embodiments. Although the following embodiments will be described as relates to ablation system 50 (FIG. 1), it is envisioned that the embodiments of the present disclosure may be modified for use with various other ablation systems.

Figure 2:
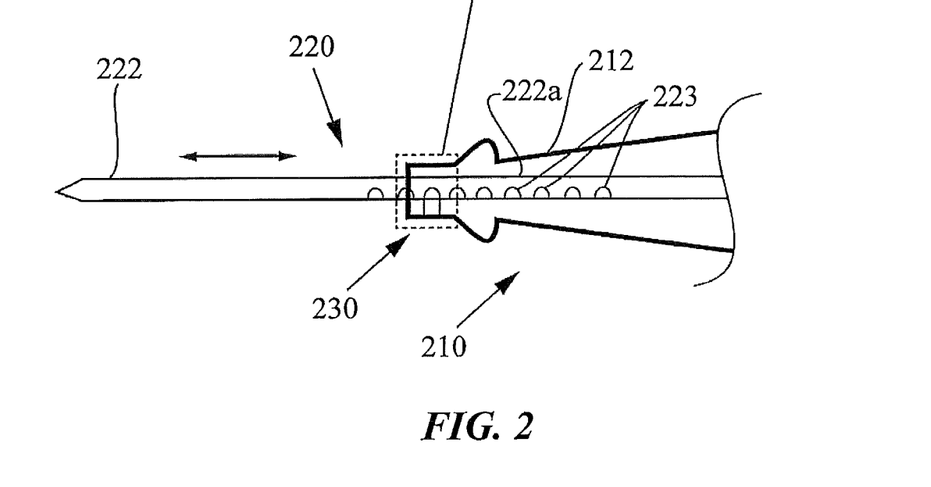
FIG. 2 is side view of the distal end of an ablation device in accordance with another embodiment of the present disclosure.
Figure 2A:
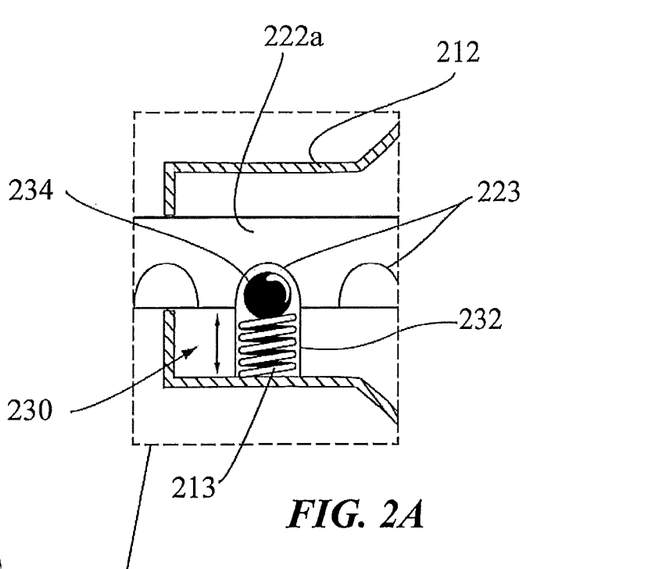
FIG. 2A is an enlarge view of the indicated portion of FIG. 2.

With reference to FIGS. 2 and 2a, in a first embodiment of an ablation device having an electrode assembly with a selectively adjustable insertable length, ablation device 200 includes an electrode assembly 220 having an electrode 222. Electrode 222 includes a plurality of detents 223 formed along a proximal end 222a thereof. Detents 223 are spaced at intervals corresponding to the desired incremental increase/decrease in the length of the insertable portion of electrode assembly 220. The closer together the spacing of detents 223 the more gradual the incremental adjustment of the insertable length of electrode assembly 220 while the further apart spacing of detents 223 the more pronounced the incremental adjustment of the insertable length of electrode assembly 220.

With continued reference to FIGS. 2 and 2A, a locking mechanism 230 is maintained within housing 212. Locking mechanism 230 is configured to selectively lock electrode assembly 220 relative to housing 212. Locking mechanism 230 includes a spring 232 and a ball 234 operably mounted on an end of spring 232. Spring 232 is received within an opening 213 of housing 212 and is configured to bias ball 234 into one of the plurality of detents 223 formed in electrode 222. Spring 232 provides a sufficient force to bias ball 234 into one of detents 223 to prohibit relative movement between electrode 222 and housing 212 during insertion of the insertable length of electrode assembly 220 into tissue during an ablation procedure. Spring 232 does not bias ball 234 so much as to prevent retraction of ball 234 from within detent 223 when a sufficient force is applied to electrode 222 relative to housing 212. Such a force may be applied by hand while gripping electrode 222 and simultaneously holding housing 212. Alternatively, electrode 222 may be retracted by engaging electrode 222 with a hard surface (not shown) while applying a longitudinal force to housing 212. As such, the insertable length of electrode assembly 220 may be adjusted as desired by the clinician to various lengths at any time during a procedure without having to replace electrode assembly 220 with an electrode assembly having a desired insertable length. In an alternative embodiment, locking mechanism 230 may include a button or lever (not shown) mounted on housing 212 that is configured to disengage ball 234 from within detent 223 to more securely retain electrode assembly 220 relative to housing 212 and/or to allow easier movement of electrode assembly 220 relative to housing 212. Housing 212 of ablation device 200 includes a pencil grip to facilitate operable engagement by a user. Alternatively, housing 212 may include a pistol grip or be configured for use with a trocar assembly or other device.

Figure 3:
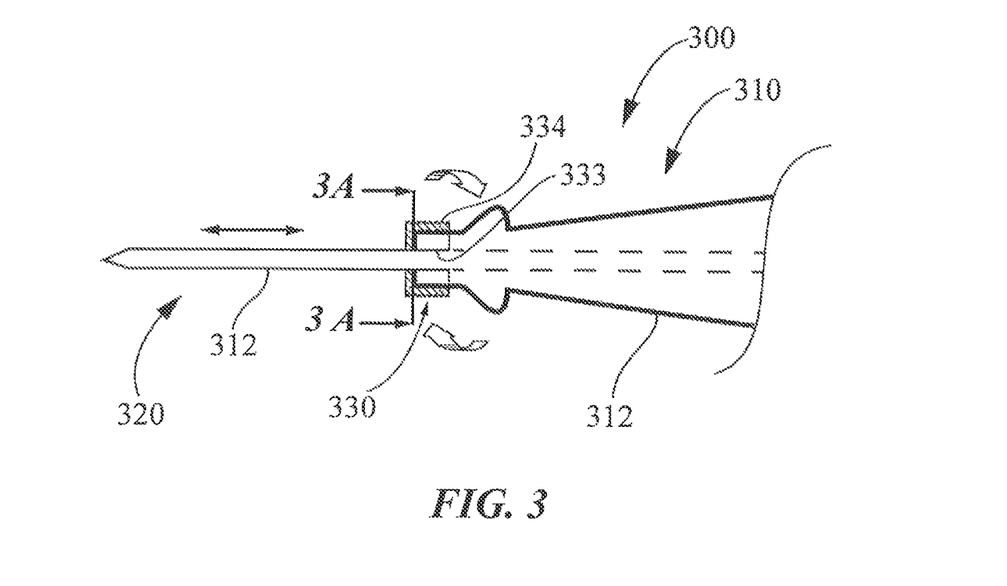
FIG. 3 is side view of the distal end of an ablation device in accordance with yet another embodiment of the present disclosure.
Figure 3A:
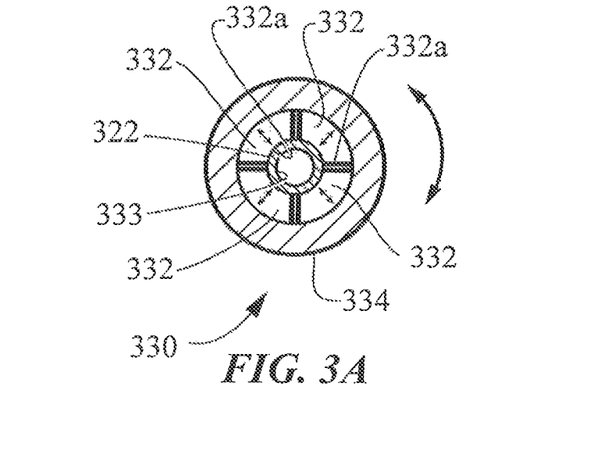
FIG. 3A is a cross-sectional end view of a distal end of the ablation device of FIG. 2 taken along line 3A-3A.

With reference now to FIGS. 3 and 3a, in another embodiment of an ablation device having an electrode assembly with a selectively adjustable insertable length, ablation device 300 includes a handle assembly 310 and an electrode assembly 320 having an electrode 320. Handle assembly 310 includes a housing 312 and a locking mechanism 330 for selectively locking electrode assembly 320 relative to housing 312. Locking mechanism 330 includes a plurality of radially spaced tapered flanges 332 formed on a distal end of housing 312. Flanges 332 collectively define a longitudinal bore 333 therethrough and include an external thread (not shown) formed thereabout. Longitudinal bore 333 is sized to selectively receive electrode 322 therethrough when flanges 332 are spaced relative to each other. The external thread is configured to engage an internal thread (not shown) of a locking nut 334. Flanges 332 are configured such that as locking nut 334 is threaded onto the external thread of flanges 332, flanges 332 are forced radially inward until internal surfaces 332a of flanges 332 engage electrode assembly 320 to selectively lock electrode assembly 320 relative to housing 312. Unthreading of locking nut 334 permits flanges 332 to return to a spaced configuration, thereby causing inner surfaces 332a of flanges 332 to disengage electrode assembly 320. As discussed above, when in a spaced configuration, throughbore 333 defined by flanges 332 is sufficiently large to permit longitudinal movement of electrode assembly 320 relative to housing 312.

Figure 4A:
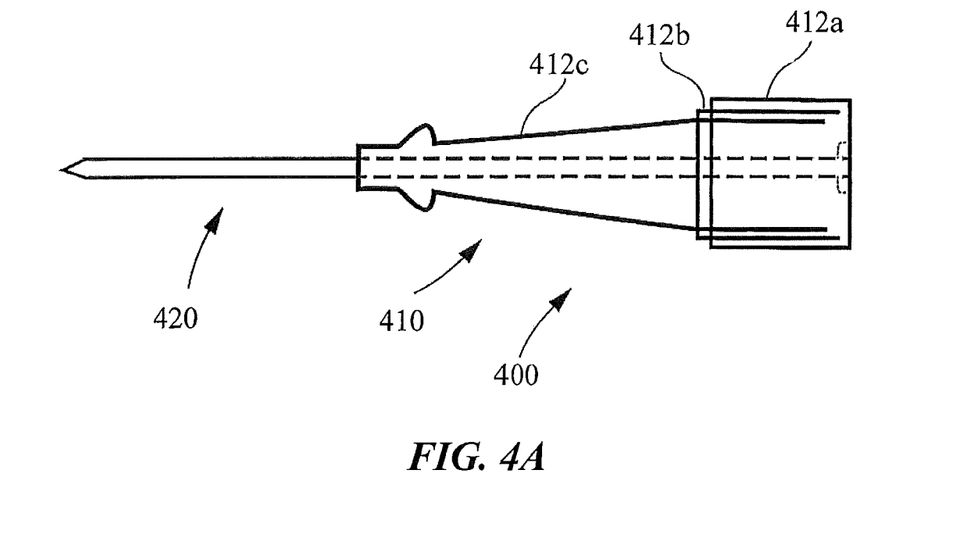
FIG. 4A is a side view of the distal end of an ablation device in accordance with still another embodiment of the present disclosure having a handle assembly in a first or fully-retracted configuration.
Figure 4B:
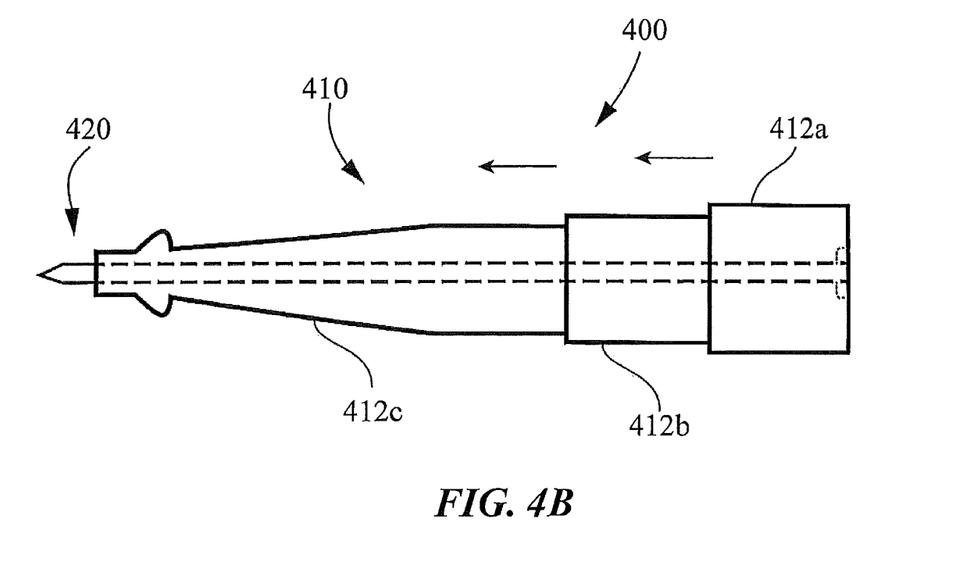
FIG. 4B is a side view of the distal end the ablation device of FIG. 4A wherein the handle assembly is in a second or fully-extended configuration.

Turning now to FIGS. 4A and 4B, in still another embodiment of an ablation device having an electrode assembly with a selectively adjustable insertable length, ablation device 400 includes a handle assembly 410 including a plurality of housing segments 412a, 412b, 412c and an electrode assembly 420. Although shown including three (3) housing segments, it is envisioned that handle assembly 410 may include only two (2) housing segments or more than three (3) housing segments. Electrode assembly 420 is fixed relative to first housing segment 412a. Second housing segment 412b is slidably disposed relative to first housing segment 412a. Third housing segment 412c is slidably disposed relative to second housing segment 412b. As shown in FIG. 4A, in a first configuration, each of second and third housing segments 412b, 412c are retracted within first housing segment 412a to provide electrode assembly 420 with a longest insertable length. As shown in FIG. 4B, each of second and third housing segments 412b, 412c are longitudinally moved or telescoped relative to first housing segment 412a to provide electrode assembly 420 with a shortest insertable length. Each of second and third housing segments 412b, 412c may be selectively telescoped relative to first housing segment 412a to provide electrode assembly 420 with insertable length between the longest length (FIG. 4A) and the shortest length (FIG. 4B). Housing segments 412a, 412b, 412c may be maintained relative to each other through a friction-fit between adjacent housing segments 412a, 412b, 412c. Alternatively, any or all of housing segments 412a, 412b, 412c may include a locking mechanism (not shown) to secure each of housing segments 412a, 412b, 412c in a longitudinally disposed relation with each other.

Figure 5:
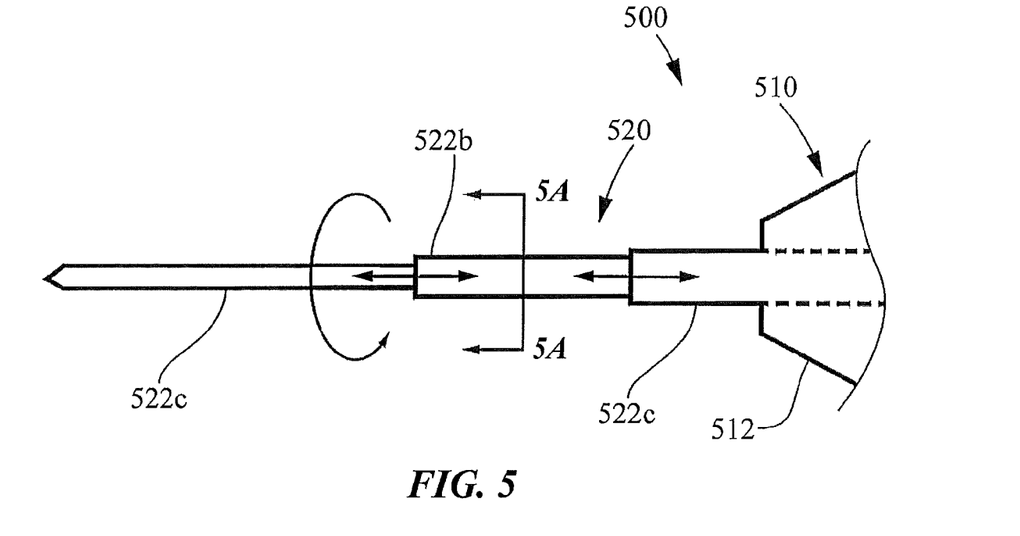
FIG. 5 is a side view of the distal end of an ablation device in accordance with still yet another embodiment of the present disclosure.
Figure 5A:
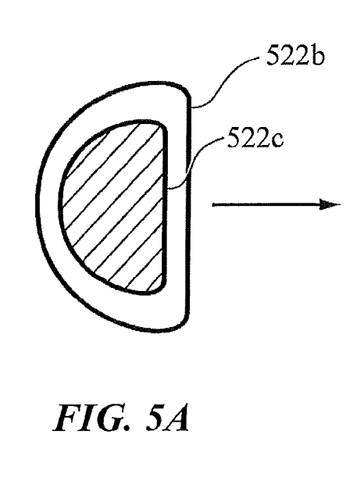
FIG. 5A is a cross-sectional end view of the ablation device of FIG. 5 taken along line 5A-5A of FIG. 5 with a third electrode segment in a first or unlocked configuration.
Figure 5B:
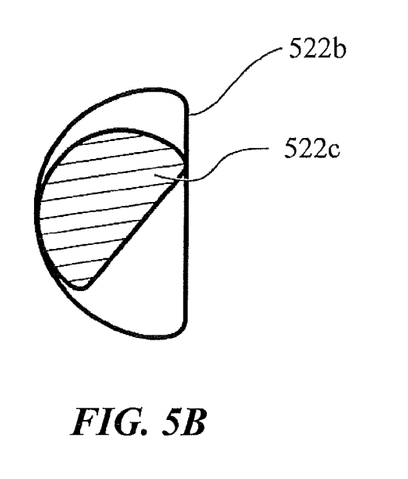
FIG. 5B is a cross-section view of FIG. 5B with the third electrode segment in a second or locked configuration.

With reference now to FIGS. 5, 5A and 5B, in yet another embodiment of an ablation device having an electrode assembly with a selectively adjustable insertable length, ablation device 500 includes an electrode assembly 520 having a plurality of electrode segments 522a, 522b, 522c. Although shown including three (3) electrode segments, it is envisioned that electrode assembly 220 may include only two (2) electrode segments or more than three (3) electrode segments. First electrode segment 522a is fixedly secured to a housing 512 of handle assembly 510. Second electrode segment 522b is slideably disposed relative to first electrode segment 522a. Third electrode segment 522c is slideably disposed relative to second electrode segment 522b.

As shown in FIGS. 5A and 5B, each of the electrode segments 522a, 522b, 522c are configured such that second and third electrode segments 522b, 522c may be rotated along a longitudinal axis within respective first and second electrode segments 522a, 522b to selectively lock second electrode segment 522b relative to first electrode segment 522a and to selectively lock third electrode segment 522c relative to second electrode segment 522b. In this manner, electrode assembly 520 includes a shortened insertable length when each of electrode segments 522a, 522b, 522c are in a first or fully-retracted position relative to one another, a lengthened insertable length when each of electrode segments 522a, 522b, 522c are in a second or fully-extended position relative to one another and electrode assembly 520 may include an insertable length anywhere in between the shortened length of the fully-retracted electrode assembly 520 and the extended length of the fully-extended electrode assembly 520. In an alternative embodiment, each of electrode segments 522a, 522c, 522c may include a plurality of notches (not shown) and/or a plurality of tabs (not shown) formed at spaced intervals along the length thereof to permit selective locking of electrode segments 522a, 522b, 522c relative to each other. The notches and/or tabs may be selectively engaged by rotation of electrode segments 522a, 522b, 522c along their longitudinal axes.

Figure 6A:
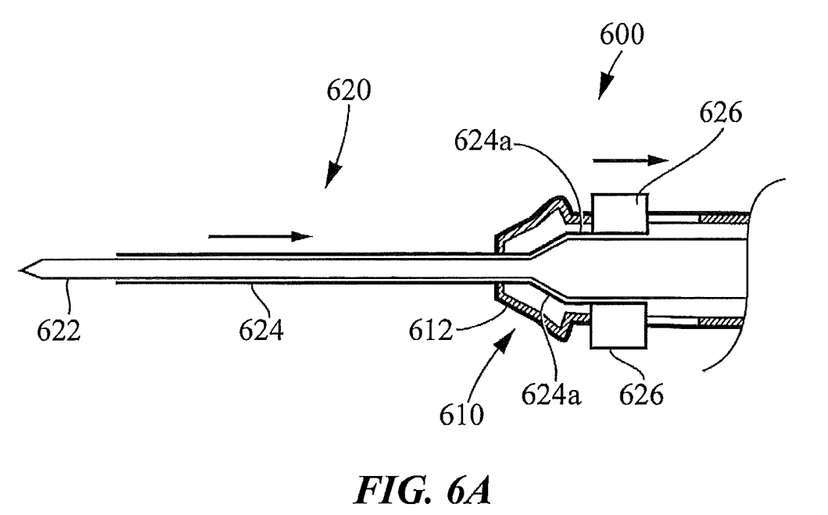
FIG. 6A is a cross-sectional side view of the distal end of an ablation device in accordance with another embodiment of the present disclosure with an insulative coating in a first or fully-extend configuration.
Figure 6B:
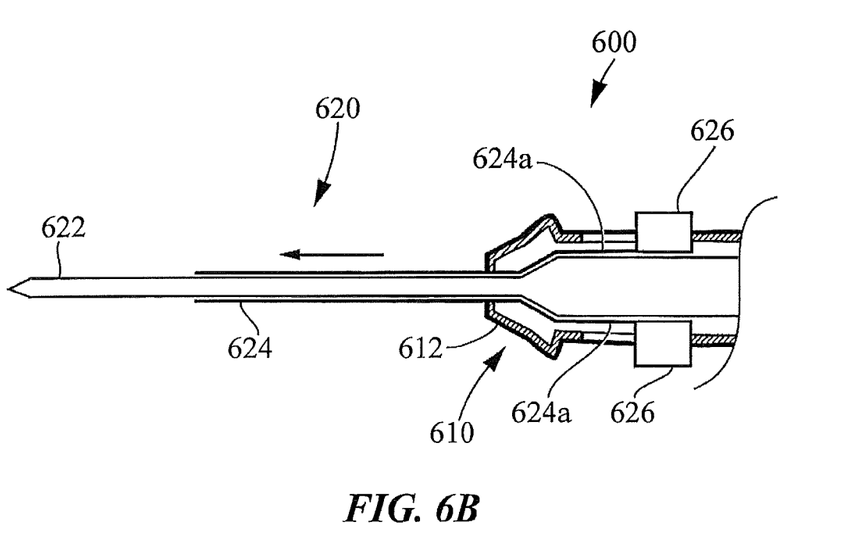
FIG. 6B is a cross-sectional side view of the distal end of the ablation device of FIG. 6A with the insulative coating in a second or fully-retracted configuration.

With reference now to FIGS. 6A and 6B, in an embodiment of an ablation device having an electrode assembly with a selectively adjustable exposed length, ablation device 600 includes a handle assembly 610 and an electrode assembly 620 having an electrode 622 and a protective layer 624. Protective layer 624 is slideably disposed along electrode 622. Protective layer 624 includes one or more tabs 626 formed at a proximal end 624a thereof for selectively retracting and advancing protective layer 624 to selectively adjust the exposed length of electrode 622. As shown in FIG. 6A, protective layer 624 is in a fully-advanced position thereby creating an exposed portion of electrode 622 having a shortened length. Turning to FIG. 6B, protective layer 624 is in a fully-retracted position thereby creating an exposed portion having a extended length. The exposed portion of electrode 622 may further include a length anywhere in between the shortened length provided by protective layer 124 in the fully-advanced position (FIG. 6A) and the lengthened length provided by protective layer 124 in the fully-retracted position (FIG. 6B). Housing 612 of handle assembly 610 may include a locking mechanism (not shown) for selectively securing protective layer 624 relative to electrode 622. Alternatively, friction between protective layer 624 and electrode 622 may be sufficient to maintain protective layer 624 in a desired position relative to electrode 622 during insertion of electrode assembly 620 into tissue.

Figure 7:
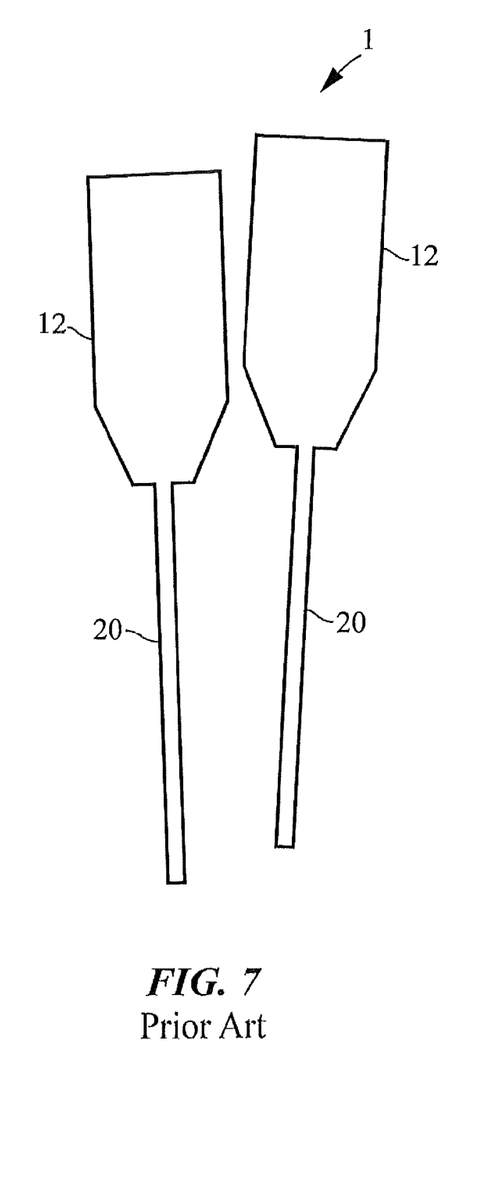
FIG. 7 is a side view of a pair of prior art ablation devices.

Turning to FIG. 7, in a prior art ablation device, housing 12 of ablation devices 1 include a diameter significantly larger then the diameter of electrode assemblies 20. As seen in FIG. 7, the large diameter of housing 12 limits the spacing between electrode assemblies 20. As such, the proximity in which electrode assemblies 20 of adjacent ablation devices 1 may be placed is limited. By reducing the diameter of the housings, i.e., housing 712 in FIG. 8, electrode assemblies 720 of adjacent ablation devices 700 may be approximated closer together to provide a more focused delivery of RF energy to the target tissue.

Figures 9, 9A:
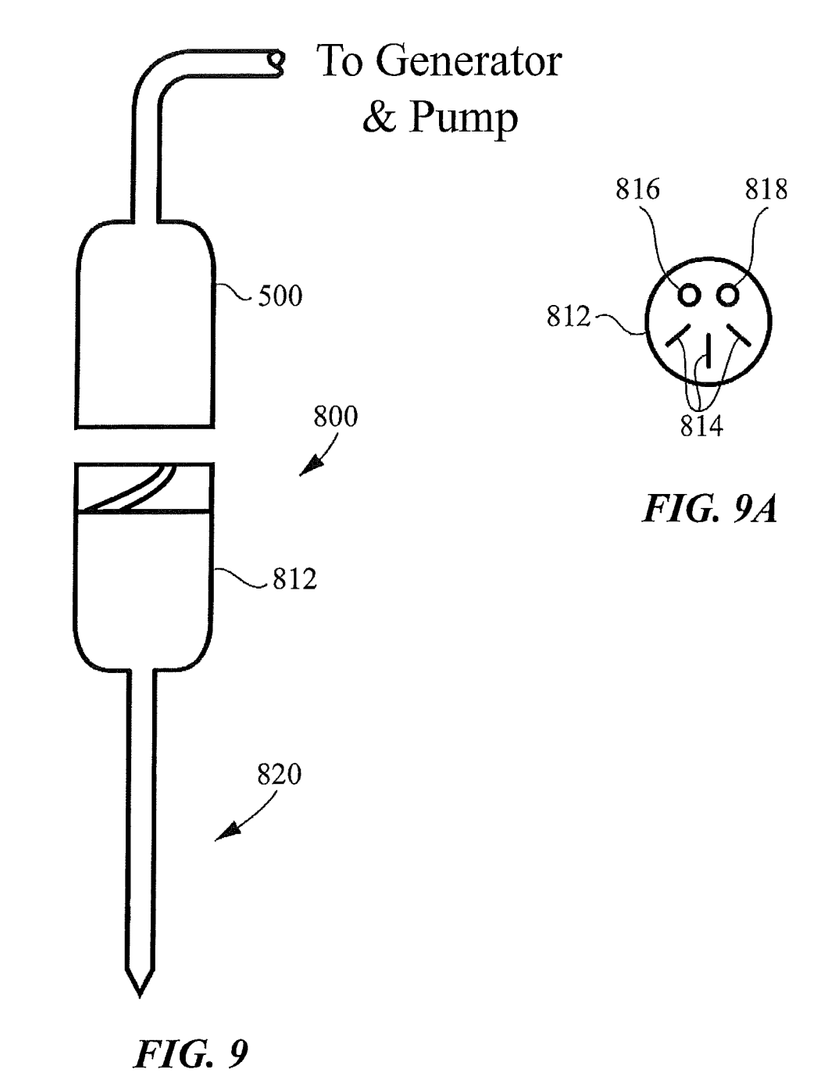
FIG. 9 is a side view of an ablation device in accordance with still another embodiment of the present disclosure.
FIG. 9A is a proximal end view of the ablation device of FIG. 9.

With reference back to FIG. 1, as shown, housing 112 includes multiple ports, e.g., electrical port 114, inlet port 116 and outlet port 118 for operable connection with, e.g., power source 52 and coolant source 58. As shown, each of ports 114, 116, 118 are spaced relative to each other to provide for separate connection with each of power source 52 and supply and return of coolant source 58. As such connecting ablation device 100 to power source 52 and coolant source 58 is time consuming and likely must be completed prior to inserting the insertable portion of electrode assembly 120 into tissue. Turning to FIGS. 9 and 9A, housing 812 of ablation device 800 includes an electric portion 814, and inlet port 816 and an outlet port 818 formed on a distal and in close proximity to one another. In this manner, each of power source 52 (FIG. 1) and coolant source 58 (FIG. 2) may be selectively connected to ablation device 800 with a single plug 50a. Plug 50a may be secured to housing 812 with a bayonet connection, threading, friction fit or any other suitable means. The single connection reduces the overall size of housing 812. Such a configuration is especially beneficial when ablation device 800 is configured for hand-held operation. It is envisioned that the single connection allows the insertable portion of electrode assembly 820 of ablation device 800 to be placed in tissue prior to connection with power source 52 and/or coolant source 58.

As discussed above, the ablation devices of the present disclosure may include multiple electrodes. Typically, each of the electrodes includes a separate housing for connection with a coolant source. As such, each of the multiple electrodes includes an inlet port for connection with a supply line for the coolant source and an outlet port for connection with a return line for the coolant source. With reference to FIGS. 10 and 10A, ablation device 900 includes a handle assembly 910 having a housing 912 and an electrode assembly 920 having a plurality of electrodes 922a, 922b, 922c. Housing 912 and electrode assembly 920 are configured such that electrodes 922a, 922b, 922c are operably connected to a source of coolant 58 (FIG. 1) through a single inlet port 914 and a single outlet 916. As detailed in FIG. 10A, fluid from a coolant source (not shown) enters electrode assembly 920 through inlet port 914 formed in first electrode 922a, flows through electrode 922a and empties directly into second electrode 922b. The fluid then flows through second electrode 922b and empties directly into third electrode 922c. The fluid then flows through third electrode 922c and out of electrode assembly 920 through outlet port 916 formed in third electrode 922c. By connecting electrodes 922a, 922b, 922c in series, the size of housing 912 may be reduced and/or the number of connections between a coolant source and housing 912 may be reduced.

Once either or both of the insertable length and the exposed length of the various electrodes have been adjusted to the desired lengths, each of ablation devices herein disclosed operate as a traditional ablation device. At any point during a surgical procedure, the length of the insertable portion and/or the length of the exposed portion of the various electrodes may be adjusted as desired by the clinician to maximize the effects of the electrodes in treating tissue.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. An ablation device comprising:
 a handle assembly defining a longitudinal axis and including:
  a first housing section;
  a second housing section coupled to the first housing section and configured to slide relative to and within the first housing section; and
  a third housing section coupled to the second housing section and configured to slide relative to and within the first and second housing sections, the second housing section slidably disposed between and relative to the first and third housing sections; and
 an electrode assembly directly connected to the first housing section and extending distally through the first, second, and third housing sections, the electrode assembly having a longitudinal length that extends distally of a distal end of the third housing section such that proximal movement of at least one of the second housing section or the third housing section relative to the electrode assembly increases the longitudinal length that extends distally of the distal end of the third housing section.

2. The device of claim 1, wherein the handle assembly is movable between an extended configuration, wherein a proximal portion of the second housing section is disposed distally of the first housing section and a proximal portion of the third housing section is disposed distally of the second housing section, and a retracted configuration, wherein the proximal portion of the second housing section is disposed within the first housing section and the proximal portion of the third housing section is disposed within the second housing section.

3. The device of claim 1, wherein the handle assembly is configured for operable connection with a cooling assembly.

4. The device of claim 1, wherein the electrode assembly is configured for operable connection with a source of radio-frequency energy.

5. The device of claim 1, wherein the handle assembly is configured for operable engagement with a trocar assembly.

6. The device of claim 1, wherein the electrode assembly has a proximal end portion that is fixed to the first housing section.

7. The device of claim 1, wherein the second housing section and the third housing section are telescopically coupled.

8. The device of claim 1, wherein the electrode assembly has a proximal portion that is fixed to a proximal wall of the first housing section.

9. The device of claim 8, wherein the proximal wall of the first housing section is disposed perpendicular to a longitudinal axis defined by the antenna assembly.

10. The device of claim 9, wherein the longitudinal axis defined by the antenna assembly is coaxial with a central longitudinal axis defined by each of the first, second, and third housing sections.

\* \* \* \* \*